United States Patent
Frail et al.

(10) Patent No.: US 10,597,314 B2
(45) Date of Patent: Mar. 24, 2020

(54) FATTY ACID BIODISPERSANT AND METHODS OF USE

(71) Applicant: General Electric Company, Schenectady, NY (US)

(72) Inventors: Paul Robert Frail, Trevose, PA (US); Gloria Jean Tafel, Trevose, PA (US); Robert Semet, Trevose, PA (US); Dorothy G. Reynolds, Trevose, PA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 404 days.

(21) Appl. No.: 15/037,474

(22) PCT Filed: Nov. 22, 2013

(86) PCT No.: PCT/US2013/071499
§ 371 (c)(1),
(2) Date: May 18, 2016

(87) PCT Pub. No.: WO2015/076830
PCT Pub. Date: May 28, 2015

(65) Prior Publication Data
US 2016/0280570 A1    Sep. 29, 2016

(51) Int. Cl.
*A01N 37/06* (2006.01)
*C02F 1/50* (2006.01)
(Continued)

(52) U.S. Cl.
CPC ............... *C02F 1/50* (2013.01); *A01N 37/06* (2013.01); *C11D 1/667* (2013.01); *C11D 3/044* (2013.01);
(Continued)

(58) Field of Classification Search
CPC .......... A61K 8/342; A61K 8/30; A61Q 11/00; A01N 35/02; A01N 31/02; A01N 37/06;
(Continued)

(56) References Cited

U.S. PATENT DOCUMENTS 6,463,363 B1   10/2002   Okuda
6,514,458 B1    2/2003   Czechowski et al.
(Continued)

FOREIGN PATENT DOCUMENTS

EP    1279400 A1    1/2003
WO    199711912 A1   4/1997
(Continued)

OTHER PUBLICATIONS

Thibane et al., "Effect of Marine Polyunsaturated Fatty Acids on Biofilm Formation of Candida albicans and Candida dubliniensis" Mar. Drugs 2010, 8, 2597-2604. (Year: 2010).*
(Continued)

*Primary Examiner* — Lucas A Stelling
(74) *Attorney, Agent, or Firm* — Wegman Hessler

(57) ABSTRACT

Methods and compositions for dispersing a biofilm in an aqueous stream using fatty acids are disclosed. The fatty acids may have the formula: $R^1$-$R^5$—$CH_3$ wherein $R^1$ is an aryl or arylalkyl, —$COR^2$, —$COOR^2$, or —$CONR^3R^4$, —$PO_3(R^2)_3$; $R^2$ is H, an alkyl, an aryl or arylalkyl, or a halide; $R^3$ and $R^4$ may be the same or different and are H, a hydroxyl, an alkyl, an aryl or arylalkyl, a halide, or a sulfo (sulfonic acid group); $R^5$ is an aliphatic chain having 2-30 carbon atoms and at least one double bond; and wherein when $R^1$ is —COOH and $R^5$ has eight carbon atoms and the FA has only one double bond, such double bond is not on the number 2 carbon.

11 Claims, 1 Drawing Sheet

(51) Int. Cl.
  C02F 1/66    (2006.01)
  C02F 1/72    (2006.01)
  C11D 1/66    (2006.01)
  C11D 3/04    (2006.01)
  C11D 3/20    (2006.01)
  C02F 103/02  (2006.01)
  C02F 1/76    (2006.01)
  C02F 103/34  (2006.01)

(52) U.S. Cl.
  CPC ........... C11D 3/046 (2013.01); C11D 3/2079 (2013.01); *C02F 1/66* (2013.01); *C02F 1/722* (2013.01); *C02F 1/76* (2013.01); *C02F 2103/023* (2013.01); *C02F 2103/34* (2013.01); *C02F 2303/20* (2013.01); *C02F 2305/04* (2013.01)

(58) Field of Classification Search
  CPC .... C02F 1/50; C02F 1/66; C02F 1/722; C02F 1/76; C02F 2103/023; C02F 2103/34; C02F 2303/20; C02F 2305/04; C11D 1/667; C11D 3/044; C11D 3/046; C11D 3/2079
  See application file for complete search history.

(56) References Cited

U.S. PATENT DOCUMENTS

| | | | | |
|---|---|---|---|---|
| 2006/0260007 | A1* | 11/2006 | Wang | A61K 31/201 800/279 |
| 2008/0317815 | A1* | 12/2008 | Davies | A01N 37/02 424/423 |
| 2010/0113319 | A1 | 5/2010 | Gerusz et al. | |
| 2011/0052655 | A1 | 3/2011 | Whitekettle et al. | |
| 2011/0123462 | A1* | 5/2011 | Mordas | A61K 8/342 424/49 |
| 2012/0052052 | A1* | 3/2012 | Xi | A01N 57/16 424/94.6 |

FOREIGN PATENT DOCUMENTS

| | | | |
|---|---|---|---|
| WO | 2008140469 | A2 | 11/2008 |
| WO | 2008143889 | A1 | 11/2008 |
| WO | WO 2011/063085 | A2 | 5/2011 |

OTHER PUBLICATIONS

The Royal Society of Chemistry, The Merck Index Monograph ID M4713 "Docosahexaenoic acid", 2013 (Year: 2013).*
The Royal Society of Chemistry, The Merck Index Monograph ID M4848 "Eicosapentaenoic acid", 2013 (Year: 2013).*
The Royal Society of Chemistry, The Merck Index Monograph ID M2331 "Benzalkonium Chloride", 2013 (Year: 2013).*
Ryan et al., "Diffusible signals and interspecies communication in bacteria", Microbiology, vol. No. 154, pp. 1845-1858, 2008.
Davies et al, "A Fatty Acid Messenger Is Responsible for Inducing Dispersion in Microbial Biofilms", Journal of Bacteriology, vol. No. 191, Issue No. 5, pp. 1393-1403, Mar. 2009.
International Search Report and Written Opinion issued in connection with corresponding PCT Application No. PCT/US2013/071499 dated Aug. 18, 2014.
Simionato, A.V.C. et al., "Characterization of a Putative '*Xylella Fastidiosa*' Diffusible Signal Factor by HRGC-EI-MS", Journal of Mass Spectrometry, vol. 42, pp. 1375-1381, 2007.
Huang, T. et al., "Extracellular Fatty Acids Facilitate Flagella-Independent Translocation by '*Stenotrophomonas maltophilia*'", Research in Microbiology, vol. 158, pp. 702-711, 2007.
Katritzky, A.R. et al., "Biguanidines, Guanylureas, and Guanylthioureas", ARKIVOC (viii), pp. 76-96, 2010.
Horn, A.F. et al., "Oxidative Stability of 70% Fish Oil-in-Water Emulsions: Impact of Emulsifiers and pH", Eur. J. Lipid Sci. Technol., vol. 113, pp. 1243-1257, 2011.
Gene Expression, Wikipedia, http://en.wikipedia.org/wiki/Gene_expression, Nov. 20, 2012, 1 page.
Quorum Sensing, Wikipedia, http://en.wikipedia.org/wiki/Quorum_sensing, Nov. 20, 2012, 1 page.
Chemistry, Wikipedia, http://en.wikipedia.org/wiki/Omega_fatty_acid, Jan. 25, 2013, 2 pages.
Fatty Acid, Wikipedia, http://en.wikipedia.org/wiki/Fatty_acid, Jan. 25, 2013, 10 pages.
Omega-7 Fatty Acid, Wikipedia, http://en.wikipedia.org/wiki/Omega-7_fatty_acid, Jan. 25, 2013, 2 pages.
Omega-9 Fatty Acid, Wikipedia, http://en.wikipedia.org/wiki/Omega-9_fatty_acid, Jan. 25, 2013, 2 pages.

* cited by examiner

US 10,597,314 B2

FATTY ACID BIODISPERSANT AND METHODS OF USE

FIELD OF THE INVENTION

Embodiments of the present invention relate to methods for reducing microbial biofilm on surfaces in contact with systems, including but not limited to, aqueous systems. More particularly, the embodiments of the present invention relate to the use of an environmentally friendly fatty acid biodispersant for reducing microbial biofilm.

BACKGROUND OF THE INVENTION

Industrial processes or operating-water systems, such as open or closed water-cycle systems, offer suitable conditions for the growth of microorganisms. Industrial processes include, but are not limited to, oil and natural gas systems and their down-hole applications and cooling water systems. Other examples of industrial systems are those systems that are found in the food and beverage industries. These water systems may form a harbor or reservoir that perpetuates growth of pathogenic microorganisms such as *Legionella pneumophila*, *Pseudomonas aeruginosa*, sulfate reducing bacteria, and other microbial fouling pathogens.

Many of these microorganisms form a slime known as biofilm on the surfaces of water-bearing systems. The biofilms offer a selective advantage to microorganisms to ensure the microorganisms' survival or to allow them a certain time to exist in a dormant state until suitable growth conditions arise. In the case of cooling water systems in particular, these biofilm deposits can lead to reduced heat exchange efficiency, pipeline damage, and corrosion within the systems. Adverse effects on process control are possible, which can ultimately reduce the efficiency of the industrial process in question and impair product quality. In addition, biofilm or slime deposits generally lead to higher energy consumption.

Control of biofilms involves the prevention of microbial attachment and the removal of existing bio-films from surfaces. While removal in many contexts is accomplished by short cleansing treatments with highly caustic or oxidizing or non-oxidizing agents, the most commonly used materials to control bio-films are biocides and biodispersants.

The deposition of the bacterial slimes may be controlled with biocides that kill off the microorganisms in the operating water and thus prevent slime production. Due to the protective nature of biofilms, however, larger concentrations are needed to penetrate the biofilm and kill the microorganisms within. Thus, biocides to control biofilm increase costs, and because of their toxicity, biocides pose considerable dangers to those handling them and to the environment.

Surfactants are also regularly applied in water treatment programs as biodispersant agents believed to play a role in the removal of organic masses from surfaces. Surfactants may also enhance biocide efficacy or assist in the water miscibility of various biocidal agents. Unfortunately, some surfactants are toxic to non-target aquatic organisms upon discharge to common receiving bodies of water or possess functional groups that have the potential to generate AOX species, such as amines and amides, and are currently regulated in European countries.

The more non-toxic surfactants often require higher levels of concentrations to achieve their purpose, thereby making them uneconomical due to the huge amount of water treated, and prone to forming high levels of unwanted foam. Foaming results in the need to feed antifoam compositions to the system. Foam, even with feeding antifoam compositions, may be problematic in some industrial applications like air separation processes.

Additionally, in many aqueous systems, such as in industrial cooling systems, scale control agents ("SCA") are added to the system water to inhibit or control scale formation that would otherwise form. Such scale forming precipitates include calcium, magnesium, and iron or copper salts and complexes. In many cases in which biofilm control agents are also added to these systems, the biofilm control agent impairs the ability of the SCA to remain dissolved or suspended in the water system. Undesirable precipitation of the SCA means that less of the SCA is available in the system water to perform its intended scale control function.

BRIEF DESCRIPTION OF THE INVENTION

It was surprisingly discovered that diffusible signal factors ("DSF"), such as fatty acids, were effective biodispersants in aqueous industrial processes. The fatty acid biodispersants are low-foaming and do not appear to impair the ability of the SCA to remain suspended in the water system. Accordingly, methods and compositions for dispersing a biofilm in an aqueous stream are disclosed.

In one embodiment, a method is disclosed for dispersing a biofilm in an aqueous stream by contacting the aqueous stream with a biodispersant composition with at least one unsaturated fatty acid which is not 2-decenoic acid ("FA") therein. The FA may be a fatty acid having a polar head group on a terminal end. The biodispersant composition optionally also comprises 2-decenoic acid.

In another embodiment, biodispersant compositions are disclosed. The biodispersant composition may have at least one unsaturated fatty acid which is not 2-decenoic acid ("FA"). The FA may have a polar head group on a terminal end, and the biodispersant composition optionally also comprises 2-decenoic acid. The biodispersant composition may further include at least one emulsifier selected from ethoxylated surfactants, alkyl alcohols, carboxylic acids, and combinations thereof and may comprise an emulsion.

DETAILED DESCRIPTION

Figure 1:
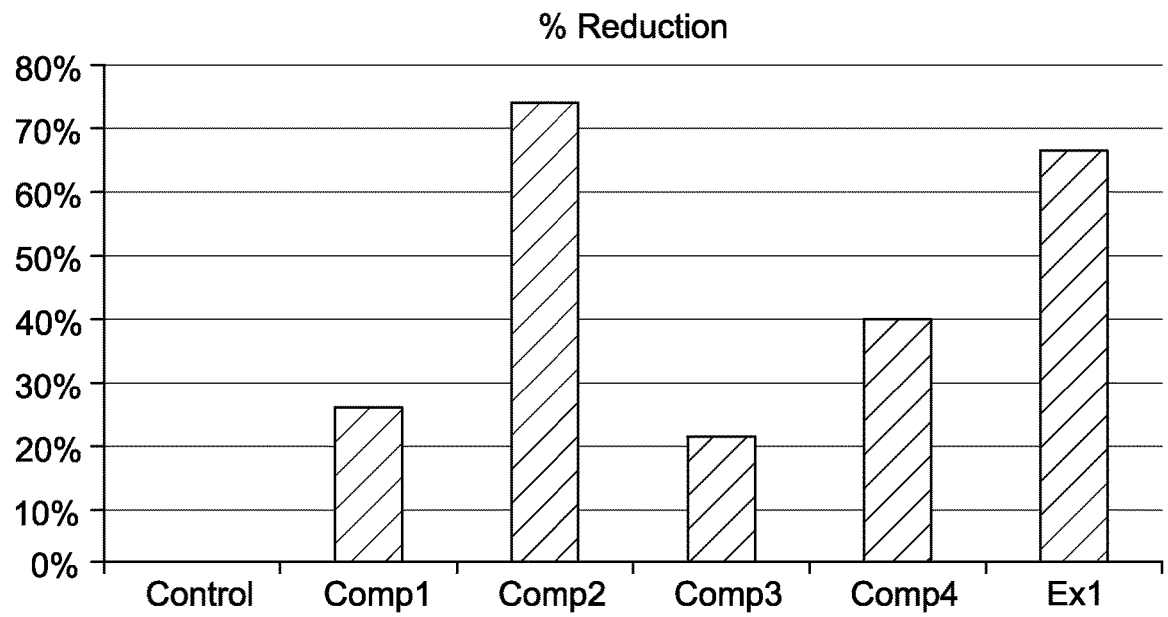
FIG. 1 is a graph showing the % Reduction results of various exemplary and comparable biodispersant compositions on biofilms in artificial cooling-water.

Many species of bacteria use quorum sensing to coordinate multiple types of behavior with other bacteria, including biofilm-forming or dispersing behavior. In the quorum sensing process, molecules called diffusible signal factors ("DSF"), act as signals to communicate bacteria behavior from cell-to-cell. It was surprisingly discovered that DSF including fatty acids were effective biodispersants in aqueous industrial processes, such as cooling-water systems including cooling towers. The fatty acid biodispersants are low-foaming and do not appear to impair the ability of SCA to remain suspended in the water system. Without limiting this disclosure to one theory of operation, it is believed that fatty acids signal the bacteria colony to disperse the biofilm and return to the planktonic state or act as quorum quenchers by disrupting signal communications. The long acid chain in fatty acids may also penetrate a biofilm and disperse it via micellar mechanisms. Accordingly, methods and compositions for dispersing a biofilm in an aqueous stream using fatty acids are disclosed. More particularly, the biofilms are at least 1 µm thick, such as 1-3000 µm, 1-1000 µm, or 10-900 µm. The biofilm may be formed by and contain bacteria. In an embodiment, the bacteria are *Pseudomonas, Burkholderia, Areomonas, Pasteurella, Pantoea, Alcaligenes* and *Sphingomonas*, as well as anaerobes such as sulfate reducers (*Desulfovibrio*) and also *Legionella.*

An article titled *A Fatty Acid Messenger Is Responsible for Inducing Dispersion in Microbial Biofilms*, published in March 2009 in the Journal of Bacteriology ("Article") is incorporated by reference herein in its entirety. The Article discloses that cis-2-decenoic acid may be used to disperse biofilms. However, the Article states that the amount of cis-2-decenoic acid which is needed for activity is 1.0 nM to 10 mM. However, testing has demonstrated that the actual amount needed is several times more than that for sufficient activity, making the use of cis-2-decenoic acid impractical. Additionally, the Article discloses that cis-2-decenoic is specific in this respect and that even trans-2-decenoic acid would not work the same since the amount of trans-2-decenoic acid needed would be in the mM range, rather than starting at the nM range. Surprisingly, embodiments of the present invention demonstrate that other fatty acids different from cis-2-decenoic acid not only work, but at much lower concentrations than cis-2-decenoic acid.

In one embodiment, a method is disclosed for dispersing a biofilm in an aqueous stream by contacting the aqueous stream with a biodispersant composition with at least one unsaturated fatty acid ("FA") which is not 2-decenoic acid. Such fatty acids can have a polar head group on a terminal end, and can optionally be used in conjunction with 2-decenoic acid, although other fatty acids are better as explained above. The polar head group may include at least one functional group selected from the group consisting of a ketone, a carboxylic acid, an amide, a phosphate, an aryl, and a cyclic aliphatic structure. Also, the at least one FA may include two or more unsaturated fatty acids, such as two or three or four or five fatty acids.

The at least one FA may have the following chemical formula:

$$R^1\text{-}R^5\text{—}CH_3$$

wherein $R^1$ is an aryl, —$COR^2$, —$COOR^2$, —$CONR^3R^4$, or —$PO_3(R^2)_3$; $R^2$ is H, an alkyl, an aryl or arylalkyl, or a halide; $R^3$ and $R^4$ may be the same or different and are H, a hydroxyl, an alkyl, an aryl or arylalkyl, a halide, or a sulfo (sulfonic acid group); $R^5$ is an aliphatic chain having 2-30 carbon atoms and at least one double bond; and wherein when $R^1$ is —COOH and $R^5$ has eight carbon atoms and the FA has only one double bond, such double bond is not on the number 2 carbon. In an embodiment, $R^5$ is an aliphatic chain having at least two double bonds, such as two or three double bonds. More particularly, $R^5$ has 9-18 carbon atoms. In an embodiment, the double bonds are present on the carbon 5 to carbon 9 positions. For purposes of this disclosure, in the structure $R^1$-$R^5$—$CH_3$, the $CH_3$ is the carbon 1 position, and the positions increase as the carbons get closer to $R^1$. Also, the FA may not have a double bond on the number 2 carbon.

The FA may be equal to or less than about 80% by weight of a total weight of the biodispersant composition. In another embodiment, the FA may range from about 20% to about 70% by weight of a total weight of the biodispersant composition. Alternatively, the FA may range from about 30% to about 60% of a total weight of the biodispersant composition.

The fatty acid may be artificially or naturally sourced and can be a cis or trans fatty acid, or a combination of both. The fatty acid may be linear or branched, more particularly linear. Naturally sourced fatty acids may come from animal or plant sources, including, but not limited to, fish oil, beef fat, krill oil, fowl fat, olive oil, palm oil, canola oil, soya oil, corn oil and seaweed. Natural sources of fatty acids are renewable and effective biodispersants with little or no health and safety concerns. These fatty acids may be considered a biodegradable or a "green" alternative to many dispersants currently used in aqueous systems. Suitable fatty acids may be unsaturated (such as polyunsaturated) fatty acids and include, but are not limited to, (Z)-tetradec-9-enoic acid, hexadec-9-enoic acid, (Z)-6-hexadecenoic acid, (9Z,11E,13E)-octadeca-9,11,13-trienoic acid, (9Z)-octadec-9-enoic acid, (E)-octadec-9-enoic acid, (E)-octadec-11-enoic acid, (9Z,12Z)-9,12-octadecadienoic acid, (9E,12E)-octadeca-9,12-dienoic acid, (9Z,12Z,15Z)-9,12,15-octadecatrienoic acid, (5Z,8Z,11Z,14Z)-5,8,11,14-eicosatetraenoic acid, (5Z,8Z,11Z,14Z,17Z)-5,8,11,14,17-icosapentaenoic acid, (Z)-docos-13-enoic acid, (4Z,7Z,10Z,13Z,16Z,19Z)-docosa-4,7,10,13,16,19-hexaenoic acid, and combinations thereof. In yet another embodiment, the biodispersant composition may comprise (9Z,11E,13E)-octadeca-9,11,13-trienoic acid, (5Z,8Z,11Z,14Z,17Z)-5,8,11,14,17-icosapentaenoic acid, and (4Z,7Z,10Z,13Z,16Z,19Z)-docosa-4,7,10,13,16,19-hexaenoic acid.

In yet another embodiment, the biodispersant composition may comprise at least one saturated or aliphatic fatty acid in addition to the unsaturated fatty acid. Suitable saturated fatty acids include, but are not limited to, octanoic acid, decanoic acid, dodecanoic acid, tetradecanoic acid, hexadecanoic acid, octadecanoic acid, icosanoic acid, docosanoic acid, tetracosanoic acid, hexacosanoic acid.

In another embodiment, the biodispersant composition may comprise water and at least one emulsifier. More particularly, the composition contains an emulsion. While the emulsion can be an oil-in-water emulsion, it may be a water-in-oil emulsion for increased concentration of the fatty acids, which would form the oil phase of the emulsion. The emulsifiers may act to disperse the FA throughout the biodispersant composition or aqueous stream being treated. The emulsifier may be an effective biodispersant by itself, or it may contribute minimally or not at all to the FA in dispersing the biofilm. Suitable emulsifiers include, but are not limited to, ethoxylated surfactants, alkyl alcohols, carboxylic acids and their analogues, such as trichlorohexanoic acid, poylamines, such as polyethyleneimine, and combinations thereof. Additional emulsifier examples include polysiloxanes, carbosilanes, dibromobutane, and dicyanobutane and combinations thereof. In another embodiment, the emulsifier may range from about 0.5% to about 30% by weight of a total weight of the biodispersant composition, such as 1%-20%, 1%-10%, and 5-10%.

An inorganic salt solution may also be added to help stabilize the emulsion and to control pH, and can comprise at least one member selected from the group consisting of an alkali or alkaline chloride, an alkali or alkaline sulfate, or combinations thereof. Suitable inorganic salt solutions include, but are not limited to, NaCl or $MgSO_4$ solutions. The inorganic salt solution may range from about 0.1 to about 30% by weight of a total weight of the biodispersant composition, such as 0.1-20%, 0.1-10%, and 0.1-1%.

A suitable ethoxylated surfactant may comprise polyethylene glycol ("PEG") polymers, polyoxyethylene-polyoxypropylene block copolymers ("EO/PO block copolymer"), polyoxyethylene sorbitan monooeleate and combinations thereof. The ethoxylated surfactant may be used from about 5% to about 10% by weight of a total weight of the biodispersant composition, although other ranges are envisioned for the emulsifiers, as disclosed above.

In yet another embodiment, the biodispersant composition may comprise at least one water-soluble pH adjusting agent. The pH adjusting agent may range from about 0.1% to about 10% by weight of a total weight of the biodispersant composition and can include, for example, one or more inorganic or organic bases, or one or more inorganic or organic acids. The inorganic bases can include one or more of NaOH, $NaHCO_3$, and $NaCO_3$. The inorganic acids can include one or more of HCl, $H_2SO_4$, and $H_3PO_4$. Organic acids may include one or more of organic sulfonates, organic phosphonates, and organic carboxylic acids. Organic bases can include one or more of amine based compounds such as methyl amines. Organic species can be single molecules or polymers.

The FA may be used in conjunction with a biocide to disperse a biofilm thereby reducing the amount of biocide required to kill the bacteria in a given aqueous system. Accordingly, in another embodiment, the biodispersant composition may further comprise at least one antimicrobial composition. The antimicrobial composition may be oxidizing or non-oxidizing biocides. Examples of non-oxidizing biocides include, but are not limited to, guanidine or biguanidine salts, quaternary ammonium salts, phosphonium salts, 2-bromo-2-nitropropane-1, 3-diol, 5-chloro-2-methyl-4-isothiazolin-3-one/2-methyl-4-isothiazolin-3-one, n-alkyl-dimethylbenzylammonium chloride, 2,2,dibromo-3-nitrilopropionamidemethylene-bis(thiocyanate), dodecyl-guanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium chloride, 4,5,-dichloro-1,2,-dithiol-3-one, sodium dimethyl-dithiocarbamate, disodium ethylenebisdithiocarbamate, Bis(trichloromethyl)sulfone, 3,5-dimethyl-tetrahydro-2H-1,3,5,-thiadiazine-2-thione, 1,2,-benzisothiazolin-3-one, decylthioethylamine hydrochloride and combinations thereof. Examples of oxidizing biocides include, but are not limited to, copper sulfate, silver nitrate, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, and combinations thereof. In yet another embodiment, the antimicrobial composition may be a polyalkylene guanidine or polyalkylene biguanidine salt biocide.

In another method embodiment, the concentration of the biodispersant composition relative to the aqueous stream treated may range from about 0.1 to about 1000 ppm by volume of the aqueous stream. In yet another embodiment, the concentration of the biodispersant composition to the aqueous stream may range from about 10 to about 100 ppm by volume of the aqueous stream. Alternatively, the concentration of the biodispersant composition to the aqueous stream may range from about 20 to about 50 ppm by volume of the aqueous stream.

In another embodiment, biodispersant compositions are disclosed. The biodispersant composition comprises at least one unsaturated fatty acid ("FA") which is not 2-decenoic acid. The fatty acid may have a polar head group on a terminal end. The biodispersant composition optionally also comprises 2-decenoic acid. The biodispersant composition may also include water and at least one emulsifier selected from ethoxylated surfactants, alkyl alcohols, carboxylic acids, and combinations thereof, and more particularly comprises an emulsion. The polar head group of the fatty acid may include at least one functional group selected from the group consisting of a ketone, a carboxylic acid, an amide, a phosphate, an aryl or arylalkyl, and a cyclic aliphatic structure. The least one FA may include two or more unsaturated fatty acids, such as two or three, or four, or five. The FA may have the following chemical formula:

$$R^1-R^5-CH_3$$

wherein $R^1$ is an aryl or arylalkyl, $-COR^2$, $-COOR^2$, or $-CONR^3R^4$, $-PO_3(R^2)_3$; $R^2$ is H, an alkyl, an aryl or arylalkyl, or a halide; $R^3$ and $R^4$ may be the same or different and are H, a hydroxyl, an alkyl, an aryl or arylalkyl, a halide, or a sulfo (sulfonic acid group); $R^5$ is an aliphatic chain having 2-30 carbon atoms and at least one double bond; and wherein when $R^1$ is $-COOH$ and $R^5$ has eight carbon atoms and the FA has only one double bond, such double bond is not on the number 2 carbon. In an embodiment, the FA has 9-18 carbon atoms. $R^5$ can be an aliphatic chain having at least two double bonds, more particularly, two double bonds or three double bonds. The double bonds may be on the C5-C9 positions. The FA may not have a double bond on the number 2 carbon.

The FA may be equal to or less than about 80% by weight of a total weight of the biodispersant composition. In another embodiment, the FA may range from about 20% to about 70% by weight of a total weight of the biodispersant composition. Alternatively, the FA may range from about 30% to about 60% of a total weight of the biodispersant composition.

Suitable fatty acids may be saturated or unsaturated fatty acids and include, but are not limited to, (Z)-tetradec-9-enoic acid, hexadec-9-enoic acid, (Z)-6-hexadecenoic acid, (9Z,11E,13E)-octadeca-9,11,13-trienoic acid, (9Z)-octadec-9-enoic acid, (E)-octadec-9-enoic acid, (E)-octadec-11-enoic acid, (9Z,12Z)-9,12-octadecadienoic acid, (9E,12E)-octadeca-9,12-dienoic acid, (9Z,12Z,15Z)-9,12,15-octadecatrienoic acid, (5Z,8Z,11Z,14Z)-5,8,11,14-eicosatetraenoic acid, (5Z,8Z,11Z,14Z,17Z)-5,8,11,14,17-icosapentaenoic acid, (Z)-docos-13-enoic acid, (4Z,7Z,10Z,13Z,16Z,19Z)-docosa-4,7,10,13,16,19-hexaenoic acid, and combinations thereof. In yet another embodiment, the biodispersant composition may comprise (9Z,11E,13E)-octadeca-9,11,13-trienoic acid, (5Z,8Z,11Z,14Z,17Z)-5,8,11,14,17-icosapentaenoic acid, and (4Z,7Z,10Z,13Z,16Z,19Z)-docosa-4,7,10,13,16,19-hexaenoic acid.

In another embodiment, the biodispersant composition may include water and an emulsion, whether oil-in-water or water-in-oil. In an embodiment, the emulsion may be a water-in-oil emulsion to have a higher concentration of the FA, which forms the oil phase of the emulsion. The composition may include at least one emulsifier. Suitable emulsifiers include, but are not limited to, ethoxylated surfactants, alkyl alcohols, carboxylic acids and their analogues, such as trichlorohexanoic acid, poylamines, such as polyethyleneimine, and combinations thereof. Additional emulsifier examples include polysiloxanes, carbosilanes, dibromobutane, and dicyanobutane, and combinations thereof. In another embodiment, the emulsifier may range from about 0.5% to about 30% by weight of a total weight of the biodispersant composition, such as 1%-20%, 1%-10%, and 5-10%.

An inorganic salt solution may also be included to stabilize the emulsion and control pH, and may comprise at least one member selected from the group consisting of an alkali or alkaline chloride, an alkali or alkaline sulfate, or combinations thereof. Suitable inorganic salt solutions include, but are not limited to, NaCl or $MgSO_4$ solutions. The inorganic salt solution may range from about 0.1 to about 30% by weight of a total weight of the biodispersant composition, such as 0.1-20%, 0.1-10%, and 0.1-1%.

A suitable ethoxylated surfactant may comprise polyethylene glycol ("PEG") polymers, polyoxyethylene-polyoxypropylene block copolymers ("EO/PO block copolymer"), polyoxyethylene sorbitan monooeleate and combinations thereof.

In yet another embodiment, the biodispersant composition may comprise at least one water-soluble pH adjusting agent. The pH adjusting agent may range from about 0.1% to about 10% by weight of a total weight of the biodispersant composition.

In another embodiment, the biodispersant composition may comprise at least one antimicrobial composition. The antimicrobial composition may be oxidizing or non-oxidizing biocides. Examples of non-oxidizing biocides include, but are not limited to, guanidine or biguanidine salts, quaternary ammonium salts, phosphonium salts, 2-bromo-2-nitropropane-1, 3-diol, 5-chloro-2-methyl-4-isothiazolin-3-one/2-methyl-4-isothiazolin-3-one, n-alkyl-dimethylbenzylammonium chloride, 2,2,dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium chloride, 4,5,-dichloro-1,2,-dithiol-3-one, sodium dimethyldithiocarbamate, disodium ethylenebisdithiocarbamate, Bis (trichloromethyl)sulfone, 3,5-dimethyl-tetrahydro-2H-1,3, 5,-thiadiazine-2-thione, 1,2,-benzisothiazolin-3-one, decylthioethylamine hydrochloride and combinations thereof. Examples of oxidizing biocides include, but are not limited to, copper sulfate, silver nitrate, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, and combinations thereof. In yet another embodiment, the antimicrobial composition may be a polyalkylene guanidine or polyalkylene biguanidine salt biocide, or a combination thereof. In yet another embodiment, the antimicrobial composition may range from about 5% to about 10% by weight of a total weight of the biodispersant composition.

EXAMPLES

To test the efficacy of the fatty acid biodispersant at reducing biofilm, biofilms were established on 316 SS coupons. First, sterilized culture containers were prepared. The containers were 1000-ml beakers charged with a magnetic stirrer and 490 ml of filtered and sterilized artificial cooling-water ("ACW"). The ACW was prepared to simulate the water typically found in industrial cooling-water systems. The ACW had the composition as in Table 1.

TABLE 1

| Component | Amount |
|---|---|
| Distilled Water | 1.0 l |
| $CaCl_2 \cdot 2H_2O$ | 1.47 g |
| $MgSO_4 \cdot 7H_2O$ | 1.23 g |
| $NaHCO_3$ | 0.637 g |
| $Na_2CO_3$ | 0.133 g |
| $NaH_2SO_4 \cdot H_2O$ | 0.0116 g |

Then, 10 ml of sterilized 30 g/l Tryptic soy broth ("TSB") was added to the beakers and mixed with the ACW to form a culture solution. Next, 50 ml of culture solution was removed from each beaker. Then 50 ml (50 ppm by volume) of a different biodispersant composition was added to each beaker.

Exemplary biodispersant compositions have the general formula as in Table 2. Fish oil was used as the fatty acid source. The fish oil comprised ≤30.0 wt % of a mixture of palmitic and stearic acids, and 20.0-31.0 wt % of an omega-3 fatty acid mixture as triglycerides. The fatty acid mixture comprised (9Z,11E,13E)-octadeca-9,11,13-trienoic acid, (5Z,8Z,11Z,14Z,17Z)-5,8,11,14,17-icosapentaenoic acid, and (4Z,7Z,10Z,13Z,16Z,19Z)-docosa-4,7,10,13,16, 19-hexaenoic acid.

TABLE 2

| Component | Amount |
|---|---|
| Fish oil (fatty acid source) | 30-60 parts by weight |
| polysorbate 80 (emulsifier) | 5-10 parts by weight |
| 0.1M NaCl solution (inorganic salt) | 30-65 parts by weight |
| Water | balance |

The different biodispersant compositions tested included an exemplary composition ("Ex1") and multiple comparative compositions (Comps 2-4) as listed in Table 3. The balance of the compositions listed was water. Comp 1 was a biodispersant composition comprising polyethylenimine ("PEI"). Comp 2 and Comp 3 were biodispersant compositions comprising ethoxylated anionic surfactants composed of alkyl substituted carboxylated acid or salt thereof and an EO/PO block copolymer as described in U.S. Pat. No. 6,514,458. Comp 2 comprised straight chain alkyl substituted carboxylated acid. Comp 3 comprise a branched alkyl substituted carboxylated acid. Comp 4 also comprised an ethoxylated anionic surfactants composed of alkyl substituted carboxylated acid or salt thereof and an EO/PO block copolymer. Comp 5 (not shown) was also tested. Comp 5 was similar to Ex1, but DI water was used in place of the fish oil. Comp 5 was not effective at removing biofilm.

TABLE 3

| Composition | Component | Amount |
|---|---|---|
| Ex1 | fish oil (fatty acid source) | 60 wt % |
|  | polysorbate 80 | 10 wt % |
|  | 0.1M NaCl solution | 25 wt % |
|  | 5N NaOH | 5 wt % |
| Comp1 | polyethyleneimine | 50 wt % |
| Comp2 | alkyl (straight chain) substituted carboxylated acid salt | 35 wt % |
|  | EO/PO block copolymer | 12.6 wt % |
| Comp3 | alkyl (branched chain) substituted carboxylated acid salt | 35 wt % |
|  | EO/PO block copolymer | 12.6 wt % |

TABLE 3-continued

| Composition | Component | Amount |
|---|---|---|
| Comp4 | alkyl substituted carboxylated acid (potassium) salt | 30-50 wt % |
| | EO/PO block copolymer | 5-20 wt % |

After adding one of the biodispersant compositions listed above to each beaker, (50 ml; 50 ppm by volume), coupon holders for each beaker were prepared for suspending the coupons vertically in the culture solution. Each coupon holder comprised a beaker lid with a means for attaching 3 rods from which the SS coupons could be attached and suspended in the culture test solution. The rods' length was chosen such that when the coupons were attached, they were fully immersed in the culture solution at an equal depth without touching the bottom of the beaker. The coupons were then aseptically suspended in the beakers and the lids were secured.

The beakers were then gently stirred for 24 hours at the same rotations per minute (rpm). After 24 hours, the coupons were removed and dipped in DI water to remove any unattached bacteria. The coupons were then removed from the rods and each coupon was placed into a 50-ml sterile polypropylene centrifuge tube containing 35 ml of sterile phosphate buffered saline (pH=7.2-7.6). Each tube was then placed in a centrifuge and vortexed on high for 1 minute. The samples were then enumerated using Petrifilm™ counts. The films were incubated at 30° C. for a minimum of 48 hours before the Colony Forming Units/ml (CFU/ml) were counted. The average CFU/ml/cm² was calculated for each composition by taking the CFU/ml for each coupon, dividing the CFU by the area of the coupon (8.77 cm²), and averaging the results. The % Reduction was then calculated as in equation 1.

$$\% \text{ Reduction} = \frac{\left(AveControl\left(\frac{CFU}{ml}/cm^2\right) - AveBDC\left(\frac{CFU}{ml}/cm^2\right)\right)}{AveControl\left(\frac{CFU}{ml}/cm^2\right)} \times 100 \quad (1)$$

wherein "AveControl" is the average CFU/ml/cm² of the control and "AveBDC" is the average CFU/ml/cm² for each biodispersant composition ("BDC"). The % Reduction for the biodispersant compositions are shown in FIG. 1.

Figure 2:
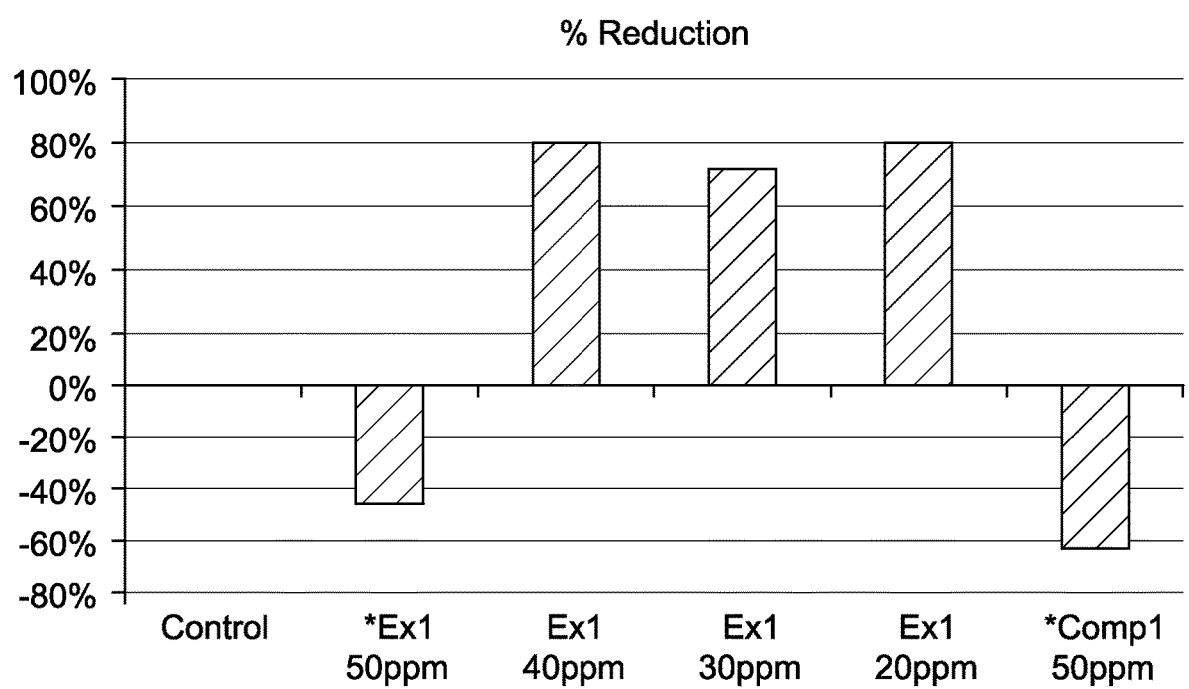
FIG. 2 is a graph showing the % Reduction results of an exemplary biodispersant composition at various concentrations and a comparative composition at 50 ppm on biofilms in artificial cooling-water.

The effectiveness of Ex1 was also tested at various concentrations in a separate set of experiments performed using the same procedure as listed above. The % Reduction of Ex1 at various concentrations is shown in FIG. 2. The data with a "*" are presumed outliers, but have been included in the interest of full disclosure.

The foaming characteristics of the biodispersant compositions listed in Table 3 were also tested. To conduct the foam tests, 50 ppm of the appropriate biodispersant composition was mix with DI water in 500 mL flask to form a test solution. Then, 200 mL of the test solution was poured into a 500 mL graduated cylinder. The cylinder was capped and shaken in an up and down motion for ten seconds (approximately 40 times). The volume of the solution and any foam therein was then measured at 0, 0.5, 1, 2, and 3 minutes. The results of the foam test are listed in Table 4.

TABLE 4

| Time (min) | Comp1 | Comp2 | Comp3 | Comp3 repeat | Comp4 | Ex1 |
|---|---|---|---|---|---|---|
| 0 | 200 | 275 | 275 | 250 | 280 | 210 |
| 0.5 | 200 | 205 | 260 | 225 | 270 | 210 |
| 1 | 200 | 200 | 250 | 220 | 270 | 210 |
| 2 | 200 | 200 | 240 | 220 | 265 | 210 |
| 3 | 200 | 200 | 230 | 220 | 260 | 210 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A biodispersant composition comprising at least one unsaturated fatty acid ("FA"), said FA having a polar head group on a terminal end, said polar head group comprising a carboxylic acid, and wherein the biodispersant composition further comprises water and at least one emulsifier selected from an ethoxylated surfactant, alkyl alcohols, carboxylic acids, and combinations thereof, wherein the at least one emulsifier comprises about 0.5% to about 30% by weight of a total weight of the biodispersant composition, and wherein the biodispersant composition comprises a water-in-oil emulsion,
wherein at least one FA is selected from the group consisting of (Z)-tetradec-9-enoic acid, hexadec-9-enoic acid, (Z)-6-hexadecenoic acid, (9Z,11E,13E)-octadeca-9,11,13-trienoic acid, (9Z)-octadec-9-enoic acid, (E)-octadec-9-enoic acid, (E)-octadec-11-enoic acid, (9Z,12Z)-9,12-octadecadienoic acid, (9E,12E)-octadeca-9,12-dienoic acid, (9Z,12Z,15Z)-9,12,15-octadecatrienoic acid, (5Z,8Z,11Z,14Z)-5,8,11,14-eicosatetraenoic acid, (5Z,8Z,11Z,14Z,17Z)-5, 8,11,14,17-icosapentaenoic acid, (Z)-docos-13-enoic acid, (4Z,7Z, 10Z,13Z,16Z,19Z)-docosa-4,7,10,13,16,19-hexaenoic acid, and combinations thereof.

2. The biodispersant composition of claim 1, wherein the at least one FA comprises two or more unsaturated fatty acids.

3. The biodispersant composition of claim 1, wherein said FA is 1-80% by weight of a total weight of said biodispersant composition.

4. The biodispersant composition of claim 1, wherein said FA comprises (9Z,11E,13E)-octadeca-9,11,13-trienoic acid, (5Z,8Z,11Z,14Z,17Z)-5,8,11, 14,17-icosapentaenoic acid, and/or (4Z,7Z,10Z,13Z,16Z,19Z)-docosa-4,7,10,13,16, 19-hexaenoic acid.

5. The biodispersant composition of claim 1, further comprising an inorganic salt solution including at least one member selected from the group consisting of an alkali or alkaline chloride, an alkali or alkaline sulfate, or combinations thereof, and wherein said ethoxylated surfactant comprises at least one selected from the group consisting of a polyethylene glycol polymer, a polyoxyethylene-polyoxypropylene block copolymer, polyoxyethylene sorbitan monooeleate and combinations thereof.

6. The biodispersant composition of claim 1, wherein said biodispersant composition further comprises at least one antimicrobial composition selected from the group consisting of guanidine or biguanidine salts, quaternary ammonium salts, phosphonium salts, 2-bromo-2-nitropropane-1, 3-diol, 5-chloro-2-methyl-4-isothiazolin-3-one/2-methyl-4-isothiazolin-3-one, n-alkyl-dimethylbenzylammonium chloride, 2,2, dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium chloride, 4,5,-dichloro-1,2,-dithiol-3-one, sodium dimethyldithiocarbamate, disodium ethylenebisdithiocarbamate, Bis(trichloromethyl) sulfone, 3,5-dimethyl-tetrahydro-2H-1,3,5, -thiadiazine-2-thione, 1,2,-benzisothiazolin-3-one, decylthioethylamine hydrochloride, copper sulfate, silver nitrate, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, trichlorohexanoic acid, and combinations thereof.

7. A method of dispersing a biofilm in an aqueous stream, said method comprising contacting an aqueous stream with a biodispersant composition containing at least one unsaturated fatty acid ("FA"), said FA comprising a fatty acid having a polar head group on a terminal end, said polar head group comprising a carboxylic acid, wherein the biodispersant composition comprises a water-in-oil emulsion, wherein said FA comprises the following chemical formula:

$R^1$-$R^5$—$CH_3$ wherein when $R^1$ is —COOH and $R^5$ is an aliphatic chain having eight carbon atoms and the FA has only one double bond, such double bond is not on the number 2 carbon, wherein the biodispersant composition provides about 60-80% reduction of biofilms.

8. The method of claim 7, wherein a concentration of said biodispersant composition relative to said aqueous stream ranges from about 0.1 to about 1000 ppm by volume of said aqueous stream.

9. The method as recited in claim 7, wherein the aqueous stream comprises water from selected from the group consisting of aqueous (i) industrial processes, (ii) operating-water systems, (iii) oil and natural gas systems, and (iv) cooling water systems.

10. The method as recited in claim 7, wherein the biodispersant composition disperses a biofilm through a micellar mechanism.

11. The method as recited in claim 7, wherein the at least one FA is selected from the group consisting of (Z)-tetradec-9-enoic acid, hexadec-9-enoic acid, (Z)-6-hexadecenoic acid, (9Z,11E,13E)-octadeca-9,11,13-trienoic acid, (9Z)-octadec-9-enoic acid, (E)-octadec-9-enoic acid, (E)-octadec-11-enoic acid, (9Z,12Z)-9,12-octadecadienoic acid, (9E, 12E)-octadeca-9,12-dienoic acid, (9Z,12Z,15Z)-9,12,15-octadecatrienoic acid, (5Z,8Z,11Z,14Z)-5,8,11,14-eicosatetraenoic acid, (5Z,8Z,11Z,14Z,17Z)-5,8,11,14,17-icosapentaenoic acid, (Z)-docos-13-enoic acid, (4Z,7Z,10Z, 13Z,16Z,19Z)-docosa-4,7,10,13,16,19-hexaenoic acid, and combinations thereof.

* * * * *